US006498018B1

(12) United States Patent
Carpenter (10) Patent No.: US 6,498,018 B1
(45) Date of Patent: *Dec. 24, 2002

(54) CULTURES OF HUMAN CNS NEURAL STEM CELLS

(75) Inventor: Melissa Carpenter, Foster City, CA (US)

(73) Assignee: Cytotherapeutics, Inc., Lincoln, RI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/486,302

(22) PCT Filed: Sep. 4, 1998

(86) PCT No.: PCT/US98/18597
§ 371 (c)(1),
(2), (4) Date: Oct. 16, 2000

(87) PCT Pub. No.: WO99/11758
PCT Pub. Date: Mar. 11, 1999

Related U.S. Application Data (63) Continuation-in-part of application No. 08/926,313, filed on Sep. 5, 1997, now Pat. No. 5,968,829.

(51) Int. Cl.[7] .............................................. C12Q 1/02
(52) U.S. Cl. ........................................ 435/29; 435/368
(58) Field of Search .............................. 435/4, 368, 6, 435/29, 467

(56) References Cited

U.S. PATENT DOCUMENTS

| | | | |
|---|---|---|---|
| 4,753,635 A | 6/1988 | Sagen et al. | 60/49 |
| 4,980,174 A | 12/1990 | Sagen et al. | 424/563 |
| 5,082,670 A | 1/1992 | Gage | 424/520 |
| 5,175,103 A | 12/1992 | Lee et al. | 435/172.3 |
| 5,411,883 A * | 5/1995 | Boss et al. | 435/240.2 |
| 5,580,777 A | 12/1996 | Bernard et al. | 435/240.2 |
| 5,612,211 A | 3/1997 | Wilson et al. | 435/378 |
| 5,639,618 A | 6/1997 | Gay | 435/7.21 |
| 5,672,499 A | 9/1997 | Anderson et al. | 435/240.2 |
| 5,688,692 A | 11/1997 | Jat | 435/354 |
| 5,750,376 A | 5/1998 | Weiss et al. | 435/69.52 |
| 5,753,506 A * | 5/1998 | Johe | 435/377 |
| 5,766,948 A | 6/1998 | Gage et al. | |
| 5,851,832 A | 12/1998 | Weiss et al. | 435/368 |
| 5,968,829 A * | 10/1999 | Carpenter | 435/467 |
| 5,980,885 A * | 11/1999 | Weiss et al. | 424/93.21 |
| 6,103,530 A * | 8/2000 | Carpenter | 435/405 |

FOREIGN PATENT DOCUMENTS

| | | |
|---|---|---|
| WO | WO 89/03872 | 5/1989 |
| WO | WO 90/06757 | 6/1990 |
| WO | WO 91/02003 | 2/1991 |
| WO | WO 91/09936 | 7/1991 |
| WO | WO 91/17141 | 11/1991 |
| WO | WO 93/01275 | 1/1993 |
| WO | WO 93/09802 | 5/1993 |
| WO | WO 94/09119 | 4/1994 |
| WO | WO 97/10292 | 5/1994 |
| WO | WO 94/16718 | 8/1994 |
| WO | WO 95/00632 | 1/1995 |
| WO | WO 96/09543 | 3/1996 |
| WO | WO-9609543 A1 * | 3/1996 |
| WO | WO 96/15226 | 5/1996 |

OTHER PUBLICATIONS

Anchan et al., "EGF and TGF–,α. Stimulate Retinal Neuroepithelial Cell Proliferation in Vitro,"Neuron, 6(6):923–936 (1991).

Andres "Removal and reimplantation of the parietal cortex of mice during the first nine days of life: consequences for the barrelfield" Journal of Neural Transplantation 1(1): 11–12 (1989) (abstract).

Blakemore & Crang., "Extensive Oligodendrocyte Remyelination Following Injection of Cultured Central Nervous System," Developmental Neuroscience, 10:1–11 (1988).

Bossart et al., "Epidermal growth factor stimulates colony formation and non–neuronal marker protein expression by human neuroblastoma in methylcellulose culture", Anticancer Res 9:1496–1504, (1989).

Calof et al., "Regulation of Neurogenesis and neuronal differentiation in primary and immortalized cells from Mouse olfactory epithellum", J. Cell Biol. 109(4 part 2): 57a, Abstract No. 307 (1989).

Calof et al., "Analysis of Neurogenesis in a Mammalian Neuroepithelium: Proliferation and Differentiation of an Olfactory Neuron Precursor in Vitro,"Neuron, 3:115–127 (1989).

Cattaneo and McKay, "Proliferation and differentiation of neuronal stem cells regulated by nerve growth factor," Nature, 347:762–765 (1990).

Cattaneo et al., "Non–virally mediated gene transfer into human central nervous system precursor cells", Mol. Brain Res., 42:161–66, (1996).

Cepko et al., "Immortalization of neural cells via retrovirus–mediated oncogene transduction," Ann. Rev. Neurosci., 12:47–65 (1989).

(List continued on next page.)

*Primary Examiner*—James Ketter
(74) *Attorney, Agent, or Firm*—Mintz, Levin, Cohn, Ferris, Glovsky and Popeo, P.C.; Ivor R. Elrifi, Esq.; Christian V. Karnakis, Esq.

(57) ABSTRACT

The invention provides a method for determining the effect of a biological agent comprising contacting a cell culture with a biological agent. The cell culture of the invention contains a culture medium containing one or more preselected growth factors effective for inducing multipotent central nervous system (CNS) neural stem cell proliferation. The cell culture also contains, suspended in the culture medium, human multipotent CNS neural stem cells that are derived from primary CNS neural tissue that have a doubling rate faster than 30 days.

4 Claims, 4 Drawing Sheets

OTHER PUBLICATIONS

Drago et al., "Fibroblast growth factor–mediated proliferation of central nervous system precursors depends on endogenous production of insulin–like growth factor I", Proc. Natl. Acad. Sci. USA 88(6): 2199–21203, (1991).

Federoff et al. "Expression of nerve growth factor in vivo from a defective herpes simplex virus 1 vector prevents effects of axotomy on sympathetic ganglia" (Proc. Natl. Acad. Sci. USA 89(5): 1636–1640, 1992).

Franklin et al., "Transplanted type–1 astrocyystes facilities repair of demyelinating lesions by host oligodendrycytes in adult rat spinal cord", Neuropathol Appl Neurobiol 17(3), 244, (1991).

Frederiksen et al., "Immortalization of precursor cells from the mammalian CNS," Neuron, 1:439–448 (1998).

Frederiksen et al., "Proliferation and differentiation of rat neuroepithelial precursor cells in vivo," The Journal of Neuroscience 8(4): 1144–1151 (1988).

Geller et al., "A Defective HSV–1 vector expresses *Escherichia coli*.62.–galactosidase in cultured peripheral neurons," Science, 241:1667–1669 (1988).

Gensburger et al., "Brain basic fibroblast growth factor stimulates the proliferation of rat neuronal precursor cells in vitro," FEBS Letts, 217(1):1–5 (1987).

Hall & Watt, "Stem cells: the generation and maintenance of cellular diversity," Development, 106:619–633 (1989).

Hammang et al., "Myelination following transplantation of EGF–responsive neural stem cells into a myelin–deficient environment", Experimental Neurology 147:84–95 (1997).

Hoffmann et al., "Transplantation of a polymer–encapsulated cell line genetically engineered to release NGF," Exp. Neurol. 122:100–106 (1993).

Hunter et al., "Growth factor responses of enriched bipotential glial progenitors," Developmental Brain Research, 54(2):235–248 (1990).

Isacson et al., "A primated model of Huntington's disease: cross–species implantation of striatal precursor cells to the excitotoxically lesioned baboon caudate–putamen", Exp. Brain Res. 75(1): 213–220, (1989).

Jaenisch et al., "The cells of primitive neuroectodermal tumours may undergo differentiation and, eventually, may be transformed to neurons, glial cells, ependymal cells", Acta Histochemica Supplementband 42:139–147, (1992).

Kaplan et al., "Neurogenesis in the 3–month–old rat visual cortex," J. Comp. Neurol., 195:323 (1981).

Kesslak et al., (Exp Neurology 94(3): 615–626, 1989).

Kumar et al. "Identification of a Set of Genes with Developmental Down–Regulated Expression in the Mouse Brain," Biochemical and Biophysical Research Comm., 185(3):1155–1161 (1992).

Lendahl et al., "CNS stem cells express a new class of intermediate filament protein," Cell, 60 585–595 (1990).

Lin et al., "GDNF: A Glial Cell Line–Derived Neurotrophic Factor Midbrain Dopaminergic Neuron,"Science, 260:1130 (1993).

Lindvall et al. "Human fetal dopamine neurons grafted into the striatum in two patients with severe Parkinson's disease", (Archives of Neurology 46(6): 615–631, 1989).

Lo et al., "V–myc Immortalizationof Early Rat Neural Crest Cells Yields a Clonal Cell Line Which Generates Both Glial and Adrenergic Progenitor Cells," Developmental Biology, 145:1390153 (1991).

Morrison et al., "Trophic stimulation of cultured neurons from neonatal rat brain by epidermal growth factor," Science, 238:72–75 (1987).

Potten & Loeffler, "Stem cells: attributes, cycles, spirals, pitfalls and uncertainties. Lessons for and from the Crypt," Development, 110:1001–1020 (1990).

Price et al., "Cell Lineage in the rat cerebral cortex: a study using retroviral–mediated gene transfer", Development 104(3): 473–482, (1988).

Raff et al., "A glial progenitor cell that develops in vitro into an astrocyte or an oligodendrocyte depending on culture medium," Nature 303:390–396 (1983).

Rakic, "Limits of neurogenesis in primates," Science 227:1054 (1985).

Reh et al., "Age of differentiation determines rat retinal germinal cell phenotype: Induction of differentiation by dissociation," The Journal of Neuroscience, 9(12):4179–4189 (1989).

Renfranz et al., "Region–specific differentiation of the hippocampal stem cell line HiB5 upon implantation into the developing mammalian brain" Cell 66:713–729 (1991).

Reynolds & Weiss., "Generation of neurons and astrocytes from isolated cells of the adult mammalian central nervous system," Science, 255:1707–1710 (1992).

Reynolds et al., "A multipotent EGF–responsive striatal embryonic progenitor cell produces neurons and astrocytes," J. Neurosci. 12(11):4565–4574 (1992).

Richardson et al., "A role for platelet–derived growth factor in normal gliogenesis in the central nervous system", Cell, 53: 309–319, 1988).

Synder et al., "Multipotent neural cell lines can engraft and participate in development of mouse cerebellum", Cell 68:33–51 (1992).

Stemple & Anderson, "Isolation of a stem cell for neurons and glia from the mammalian neural crest", Cell 71:1–20, (1992).

Temple et al., "Division and differentiation of isolated CNS blast cells in microculture," Nature, 340:471–473 (1989).

Tohyama et al., "Nestin expression in embryonic human neuroepithelium and in human neuroepithelial tumor cells", Lab. Invest., 66: 303–313, (1992).

Vescovi et al., "Continual proliferation of EGF–dependent progenitor cells of the embyronic human CNS in vitro", Society for Neuroscience Abstracts, vol. 19, Abstract #360.12 (1993).

Wendt et al. "Regeneration of rat hippocampal fimbria fibers after fimbria transection and peripheral nerve or fetal hippocampal implantation.", (Exp. Neurology 79(2): 452–461, 1983).

Yamada et al., Growth of cells in hormonally defined media—Book A Cold Spring Harbor Laboratory, 1982—Cold Spring Harbor conferences on cell proliferation, vol. 9, 131–143.

Brŋstle et al., "Chimeric brains generated by intraventricular transplantation of fetal human brain cells in embryonic rats" Nature Biotechnol. 16: 1040–1044 (1998).

Flax et al., "Engraftable human neural stem cells respond to developmental cues, replace neurons, and express foreign genes" Nature Biotechnol. 16: 1033–1039 (1998).

Weiss, "Brain cell that multiplies is isolated" The Washington Post, Oct. 31, 1998, p. A3.

Zigova & Sanberg, "The rising star of neural stem cell research" Nature Biotechnol. 16: 1007–1008 (1998).

* cited by examiner

CULTURES OF HUMAN CNS NEURAL STEM CELLS

RELATED APPLICATIONS

This application is the national stage application of PCT published application WO 99/11758, filed Sep. 4, 1998, which is a continuation-in-part of U.S. Ser. No. 08/926,313, filed Sep. 5, 1997, now U.S. Pat. No. 5,968,829, both of which are incorporated herein by reference in their entireties.

TECHNICAL FIELD OF THE INVENTION

This invention relates to isolation of human central nervous system stem cells, and methods and media for proliferating, differentiating and transplanting them.

BACKGROUND OF THE INVENTION

During development of the central nervous system ("CNS"), multipotent precursor cells, also known as neural stem cells, proliferate, giving rise to transiently dividing progenitor cells that eventually differentiate into the cell types that compose the adult brain. Stem cells (from other tissues) have classically been defined as having the ability to self-renew (i.e., form more stem cells), to proliferate, and to differentiate into multiple different phenotypic lineages. In the case of neural stem cells this includes neurons, astrocytes and oligodendrocytes. For example, Potten and Loeffler (Development, 110:1001, 1990) define stem cells as "undifferentiated cells capable of a) proliferation, b) self-maintenance, c) the production of a large number of differentiated functional progeny, d) regenerating the tissue after injury, and e) a flexibility in the use of these options."

These neural stem cells have been isolated from several mammalian species, including mice, rats, pigs and humans. See, e.g., WO 93/01275, WO 94/09119, WO 94/10292, WO 94/16718 and Cattaneo et al., *Mol. Brain Res.*, 42, pp. 161–66 (1996), all herein incorporated by reference.

Human CNS neural stem cells, like their rodent homologues, when maintained in a mitogen-containing (typically epidermal growth factor or epidermal growth factor plus basic fibroblast growth factor), serum-free culture medium, grow in suspension culture to form aggregates of cells known as "neurospheres". In the prior art, human neural stem cells have doubling rates of about 30 days. See, e.g., Cattaneo et al., *Mol Brain Res.*, 42, pp. 161–66 (1996). Upon removal of the mitogen(s) and provision of a substrate, the stem cells differentiate into neurons, astrocytes and oligodendrocytes. In the prior art, the majority of cells in the differentiated cell population have been identified as astrocytes, with very few neurons (<10%) being observed.

There remains a need to increase the rate of proliferation of neural stem cell cultures. There also remains a need to increase the number of neurons in the differentiated cell population. There further remains a need to improve the viability of neural stem cell grafts upon implantation into a host.

SUMMARY OF THE INVENTION

This invention provides novel human central nervous system stem cells, and methods and media for proliferating, differentiating and transplanting them. In one embodiment, this invention provides novel human stem cells with a doubling rate of between 5–10 days, as well as defined growth media for prolonged proliferation of human neural stem cells. In another embodiment, this invention provides a defined media for differentiation of human neural stem cells so as to enrich for neurons, oligodendrocytes, astrocytes, or a combination thereof. The invention also provides differentiated cell populations of human neural stem cells that provide previously unobtainable large numbers of neurons, as well as astrocytes and oligodendrocytes. This invention also provides novel methods for transplanting neural stem cells that improve the viability of the graft upon implantation in a host.

DETAILED DESCRIPTION OF THE INVENTION

This invention relates to isolation, characterization, proliferation, differentiation and transplantation of CNS neural stem cells.

The neural stem cells described and claimed in the applications may be proliferated in suspension culture or in adherent culture. When the neural stem cells of this invention are proliferating as neurospheres, human nestin antibody may be used as a marker to identify undifferentiated cells. The proliferating cells show little GFAP staining and little β-tubulin staining (although some staining might be present due to diversity of cells within the spheres).

When differentiated, most of the cells lose their nestin positive immunoreactivity. In particular, antibodies specific for various neuronal or glial proteins may be employed to identify the phenotypic properties of the differentiated cells. Neurons may be identified using antibodies to neuron specific enolase ("NSE"), neurofilament, tau, beta-tubulin, or other known neuronal markers. Astrocytes may be identified using antibodies to glial fibrillary acidic protein ("GFAP"), or other known astrocytic markers. Oligodendrocytes may be identified using antibodies to galactocerebroside, O4, myelin basic protein ("MBP") or other known oligodendrocytic markers. Glial cells in general may be identified by staining with antibodies, such as the M2 antibody, or other known glial markers.

In one embodiment the invention provides novel human CNS stem cells isolated from the forebrain. We have isolated 4 neural stem cell lines from human forebrain, all of which exhibit neural stem cell properties; namely, the cells are self renewing, the cells proliferate for long periods in mitogen containing serum free medium, and the cells, when differentiated, comprise a cell population of neurons, astrocytes and oligodendrocytes. These cells are capable of doubling every 5–10 days, in contrast with the prior art diencephalon-derived human neural stem cells. Reported proliferation rates of diencephalon-derived human neural stem cells approximate one doubling every 30 days. See Cattaneo et al., *Mol. Brain Res.*, 42, pp. 161–66 (1996).

Any suitable tissue source may be used to derive the neural stem cells of this invention. Neural stem cells can be induced to proliferate and differentiate either by culturing the cells in suspension or on an adherent substrate. See, e.g., U.S. Pat. Nos. 5,750,376 and 5,753,506 (both incorporated herein by reference in their entirety), and prior art medium described therein. Both allografts and autografts are contemplated for transplantation purposes.

This invention also provides a novel growth media for proliferation of neural stem cells. Provided herein is a serum-free or serum-depleted culture medium for the short term and long term proliferation of neural stem cells.

A number of serum-free or serum-depleted culture media have been developed due to the undesirable effects of serum which can lead to inconsistent culturing results. See, e.g., WO 95/00632 (incorporated herein by reference), and prior art medium described therein.

Prior to development of the novel media described herein, neural stem cells have been cultured in serum-free media containing epidermal growth factor ("EGF") or an analog of EGF, such as amphiregulin or transforming growth factor alpha ("TGF-α"), as the mitogen for proliferation. See, e.g., WO 93/01275, WO 94/16718, both incorporated herein by reference. Further, basic fibroblast growth factor ("bFGF") has been used, either alone, or in combination with EGF, to enhance long term neural stem cell survival.

The improved medium according to this invention, which contains leukemia inhibitory factor ("LIF"), markedly and unexpectedly increases the rate of proliferation of neural stem cells, particularly human neural stem cells.

We have compared growth rates of the forebrain-derived stem cells described herein in the presence and absence of LIF; unexpectedly we have found that LIF dramatically increases the rate of cellular proliferation in almost all cases.

The medium according to this invention comprises cell viability and cell proliferation effective amounts of the following components:

(a) a standard culture medium being serum-free (containing 0–0.49% serum) or serum-depleted (containing 0.5–5.0% serum), known as a "defined" culture medium, such as Iscove's modified Dulbecco's medium ("IMDM"), RPMI, DMEM, Fischer's, alpha medium, Leibovitz's, L-15, NCTC, F-10, F-12, MEM and McCoy's;

(b) a suitable carbohydrate source, such as glucose;

(c) a buffer such as MOPS, HEPES or Tris, preferably HEPES;

(d) a source of hormones including insulin, transferrin, progesterone, selenium, and putrescine;

(e) one or more growth factors that stimulate proliferation of neural stem cells, such as EGF, bFGF, PDGF, NGF, and analogs, derivatives and/or combinations thereof, preferably EGF and bFGF in combination;

(f) LIF

Standard culture media typically contains a variety of essential components required for cell viability, including inorganic salts, carbohydrates, hormones, essential amino acids, vitamins, and the like. We prefer DMEM or F-12 as the standard culture medium, most preferably a 50/50 mixture of DMEM and F-12. Both media are commercially available (DMEM—Gibco 12100-046; F-12—Gibco 21700-075). A premixed formulation is also commercially available (N2—Gibco 17502-030). It is advantageous to provide additional glutamine, preferably at about 2 mM. It is also advantageous to provide heparin in the culture medium. Preferably, the conditions for culturing should be as close to physiological as possible. The pH of the culture medium is typically between 6–8, preferably about 7, most preferably about 7.4. Cells are typically cultured between 30–40° C., preferably between 32–38° C., most preferably between 35–37° C. Cells are preferably grown in 5% $CO_2$. Cells are preferably grown in suspension culture.

In one exemplary embodiment, the neural stem cell culture comprises the following components in the indicated concentrations:

| Component | Final Concentration |
|---|---|
| 50/50 mix of DMEM/F-12 | 0.5–2.0 X, preferably 1X |
| glucose | 0.2–1.0%, preferably 0.6% w/v |
| glutamine | 0.1–10 mM, preferably 2 mM |
| $NaHCO_3$ | 0.1–10 mM, preferably 3 mM |
| HEPES | 0.1–10 mM, preferably 5 mM |
| apo-human transferrin (Sigma T-2252) | 1–1000 µg/ml, preferably 100 µg/ml |
| human insulin (Sigma I-2767) | 1–100, preferably 25 µg/ml |
| putrescine (Sigma P-7505) | 1–500, preferably 60 µM |
| selenium (Sigma S-9133) | 1–100, preferably 30 nM |
| progesterone (Sigma P-6149) | 1–100, preferably 20 nM |
| human EGF (Gibco 13247-010) | 0.2–200, preferably 20 ng/ml |
| human bFGF (Gibco 13256-029) | 0.2–200, preferably 20 ng/ml |
| human LIF (R&D Systems 250-L) | 0.1–500, preferably 10 ng/ml |
| heparin (Sigma H-3149) | 0.1–500, preferably 2 µg/ml |
| $CO_2$ | preferably 5% |

Serum albumin may also be present in the instant culture medium—although the present medium is generally serum-depleted or serum-free (preferably serum-free), certain serum components which are chemically well defined and highly purified (>95%), such as serum albumin, may be included.

The human neural stem cells described herein may be cryopreserved according to routine procedures. We prefer cryopreserving about one to ten million cells in "freeze" medium which consists of proliferation medium (absent the growth factor mitogens), 10% BSA (Sigma A3059) and 7.5% DMSO. Cells are centrifuged. Growth medium is aspirated and replaced with freeze medium. Cells are resuspended gently as spheres, not as dissociated cells. Cells are slowly frozen, by, e.g., placing in a container at −80° C. Cells are thawed by swirling in a 37° C. bath, resuspended in fresh proliferation medium, and grown as usual.

In another embodiment, this invention provides a differentiated cell culture containing previously unobtainable large numbers of neurons, as well as astrocytes and oligodendrocytes. In the prior art, typically the differentiated human diencephalon-derived neural stem cell cultures formed very few neurons (i.e., less than 5–10%). According to this methodology, we have routinely achieved neuron concentrations of between 20% and 35% (and much higher in other cases) in differentiated human forebrain-derived neural stem cell cultures. This is highly advantageous as it permits enrichment of the neuronal population prior to implantation in the host in disease indications where neuronal function has been impaired or lost.

Further, according to the methods of this invention, we have achieved differentiated neural stem cell cultures that are highly enriched in GABA-ergic neurons. Such GABA-ergic neuron enriched cell cultures are particularly advantageous in the potential therapy of excitotoxic neurodegenerative disorders, such as Huntington's disease or epilepsy.

In order to identify the cellular phenotype either during proliferation or differentiation of the neural stem cells, various cell surface or intracellular markers may be used.

When the neural stem cells of this invention are proliferating as neurospheres, we contemplate using human nestin antibody as a marker to identify undifferentiated cells. The proliferating cells should show little GFAP staining and little β-tubulin staining (although some staining might be present due to diversity of cells within the spheres).

When differentiated, most of the cells lose their nestin positive immunoreactivity. In particular, antibodies specific for various neuronal or glial proteins may be employed to identify the phenotypic properties of the differentiated cells. Neurons may be identified using antibodies to neuron specific enolase ("NSE"), neurofilament, tau, β-tubulin, or other known neuronal markers. Astrocytes may be identified using antibodies to glial fibrillary acidic protein ("GFAP"), or other known astrocytic markers. Oligodendrocytes may be identified using antibodies to galactocerebroside, O4, myelin basic protein ("MBP") or other known oligodendrocytic markers.

It is also possible to identify cell phenotypes by identifying compounds characteristically produced by those phenotypes. For example, it is possible to identify neurons by the production of neurotransmitters such as acetylcholine, dopamine, epinephrine, norepinephrine, and the like.

Specific neuronal phenotypes can be identified according to the specific products produced by those neurons. For example, GABA-ergic neurons may be identified by their production of glutamic acid decarboxylase ("GAD") or GABA. Dopaminergic neurons may be identified by their production of dopa decarboxylase ("DDC"), dopamine or tyrosine hydroxylase ("TH"). Cholinergic neurons may be identified by their production of choline acetyltransferase ("ChAT"). Hippocampal neurons may be identified by staining with NeuN. It will be appreciated that any suitable known marker for identifying specific neuronal phenotypes may be used.

The human neural stem cells described herein can be genetically engineered or modified according to known methodology. The term "genetic modification" refers to the stable or transient alteration of the genotype of a cell by intentional introduction of exogenous DNA. DNA may be synthetic, or naturally derived, and may contain genes, portions of genes, or other useful DNA sequences. The term "genetic modification" is not meant to include naturally occurring alterations such as that which occurs through natural viral activity, natural genetic recombination, or the like.

A gene of interest (i.e., a gene that encodes a biologically active molecule) can be inserted into a cloning site of a suitable expression vector by using standard techniques. These techniques are well known to those skilled in the art. See, e.g., WO 94/16718, incorporated herein by reference.

The expression vector containing the gene of interest may then be used to transfect the desired cell line. Standard transfection techniques such as calcium phosphate co-precipitation, DEAE-dextran transfection, electroporation, biolistics, or viral transfection may be utilized. Commercially available mammalian transfection kits may be purchased from e.g., Stratagene. Human adenoviral transfection may be accomplished as described in Berg et al. *Exp. Cell Res.,* 192, pp. (1991). Similarly, lipofectamine-based transfection may be accomplished as described in Cattaneo, *Mol. Brain Res.,* 42, pp. 161–66 (1996).

A wide variety of host/expression vector combinations may be used to express a gene encoding a biologically active molecule of interest. See, e.g., U.S. Pat. No. 5,545,723, herein incorporated by reference, for suitable cell-based production expression vectors.

Increased expression of the biologically active molecule can be achieved by increasing or amplifying the transgene copy number using amplification methods well known in the art. Such amplification methods include, e.g., DHFR amplification (see, e.g., Kaufman et al., U.S. Pat. No. 4,470,461) or glutamine synthetase ("GS") amplification (see, e.g., U.S. Pat. No. 5,122,464, and European published application EP 338,841), all herein incorporated by reference.

In another embodiment, the genetically modified neural stem cells are derived from transgenic animals.

When the neural stem cells are genetic modified for the production of a biologically active substance, the substance will preferably be useful for the treatment of a CNS disorder. We contemplate genetically modified neural stem cells that are capable of secreting a therapeutically effective biologically active molecule in patients. We also contemplate producing a biologically active molecule with growth or trophic effect on the transplanted neural stem cells. We further contemplate inducing differentiation of the cells towards neural cell lineages. The genetically modified neural stem cells thus provide cell-based delivery of biological agents of therapeutic value.

The neural stem cells described herein, and their differentiated progeny may be immortalized or conditionally immortalized using known techniques. We prefer conditional immortalization of stem cells, and most preferably conditional immortalization of their differentiated progeny. Among the conditional immortalization techniques contemplated are Tet-conditional immortalization (see WO 96/31242, incorporated herein by reference), and Mx-1 conditional immortalization (see WO 96/02646, incorporated herein by reference).

This invention also provides methods for differentiating neural stem cells to yield cell cultures enriched with neurons to a degree previously unobtainable. According to one protocol, the proliferating neurospheres are induced to differentiate by removal of the growth factor mitogens and LIF, and provision of 1% serum, a substrate and a source of ionic charges (e.g., glass cover slip covered with poly-omithine or extracellular matrix components). The preferred base medium for this differentiation protocol, excepting the growth factor mitogens and LIF, is otherwise the same as the proliferation medium. This differentiation protocol produces a cell culture enriched in neurons. According to this protocol, we have routinely achieved neuron concentrations of between 20% and 35% in differentiated human forebrain-derived neural stem cell cultures.

According to a second protocol, the proliferating neurospheres are induced to differentiate by removal of the growth factor mitogens, and provision of 1% serum, a substrate and a source of ionic charges (e.g., glass cover slip covered with poly-ornithine or extracellular matrix components), as well as a mixture of growth factors including PDGF, CNTF, IGF-1, LIF, forskolin, T-3 and NT-3. The cocktail of growth factors may be added at the same time as the neurospheres are removed from the proliferation medium, or may be added to the proliferation medium and the cells pre-incubated with the mixture prior to removal from the mitogens. This protocol produces a cell culture highly enriched in neurons and enriched in oligodendrocytes. According to this protocol, we have routinely achieved neuron concentrations of higher than 35% in differentiated human forebrain-derived neural stem cell cultures.

The presence of bFGF in the proliferation media unexpectedly inhibits oligodendrocyte differentiation capability. bFGF is trophic for the oligodendrocyte precursor cell line. Oligodendrocytes are induced under differentiation conditions when passaged with EGF and LIF in proliferating media, without bFGF.

The human stem cells of this invention have numerous uses, including for drug screening, diagnostics, genomics and transplantation. Stem cells can be induced to differentiate into the neural cell type of choice using the appropriate media described in this invention. The drug to be tested can be added prior to differentiation to test for developmental inhibition, or added post-differentiation to monitor neural cell-type specific reactions.

The cells of this invention may be transplanted "naked" into patients according to conventional techniques, into the CNS, as described for example, in U.S. Pat. Nos. 5,082,670 and 5,618,531, each incorporated herein by reference, or into any other suitable site in the body.

In one embodiment, the human stem cells are transplanted directly into the CNS. Parenchymal and intrathecal sites are contemplated. It will be appreciated that the exact location in the CNS will vary according to the disease state.

Implanted cells may be labeled with bromodeoxyuridine (BrdU) prior to transplantation. We have observed in various experiments that cells double stained for a neural cell marker and BrdU in the various grafts indicate differentiation of BrdU stained stem cells into the appropriate differentiated neural cell type (see Example 9). Transplantation of human forebrain derived neural stem cells to the hippocampus produced neurons that were predominantly NeuN staining but GABA negative. The NeuN antibody is known to stain neurons of the hippocampus. GABA-ergic neurons were formed when these same cell lines were transplanted into the striatum. Thus, transplanted cells respond to environmental clues in both the adult and the neonatal brain.

According to one aspect of this invention, provided herein is methodology for improving the viability of transplanted human neural stem cells. In particular, we have discovered that graft viability improves if the transplanted neural stem cells are allowed to aggregate, or to form neurospheres prior to implantation, as compared to transplantation of dissociated single cell suspensions. We prefer transplanting small sized neurospheres, approximately 10–500 $\mu$m in diameter, preferably 40–50 $\mu$m in diameter. Alternatively, we prefer spheres containing about 5–100, preferably 5–20 cells per sphere. We contemplate transplanting at a density of about 10,000–1,000,000 cells per $\mu$l, preferably 25,000–500,000 cells per $\mu$l.

The cells may also be encapsulated and used to deliver biologically active molecules, according to known encapsulation technologies, including microencapsulation (see, e.g., U.S. Pat. Nos. 4,352,883; 4,353,888; and 5,084,350, herein incorporated by reference), (b) macroencapsulation (see, e.g., U.S. Pat. Nos. 5,284,761, 5,158,881, 4,976,859 and 4,968,733 and published PCT patent applications WO92/19195, WO 95/05452, each incorporated herein by reference).

If the human neural stem cells are encapsulated, we prefer macroencapsulation, as described in U.S. Pat. Nos. 5,284,761; 5,158,881; 4,976,859; 4,968,733; 5,800,828 and published PCT patent application WO 95/05452, each incorporated herein by reference. Cell number in the devices can be varied; preferably each device contains between $10^3$–$10^9$ cells, most preferably $10^5$ to $10^7$ cells. A large number of macroencapsulation devices may be implanted in the patient; we prefer between one to 10 devices.

In addition, we also contemplate "naked" transplantation of human stem cells in combination with a capsular device wherein the capsular device secretes a biologically active molecule that is therapeutically effective in the patient or that produces a biologically active molecule that has a growth or trophic effect on the transplanted neural stem cells, or that induces differentiation of the neural stem cells towards a particular phenotypic lineage.

The cells and methods of this invention may be useful in the treatment of various neurodegenerative diseases and other disorders. It is contemplated that the cells will replace diseased, damaged or lost tissue in the host. Alternatively, the transplanted tissue may augment the function of the endogenous affected host tissue. The transplanted neural stem cells may also be genetically modified to provide a therapeutically effective biologically active molecule.

Excitotoxicity has been implicated in a variety of pathological conditions including epilepsy, stroke, ischemia, and neurodegenerative diseases such as Huntington's disease, Parkinson's disease and Alzheimer's disease. Accordingly, neural stem cells may provide one means of preventing or replacing the cell loss and associated behavioral abnormalities of these disorders. Neural stem cells may replace cerebellar neurons lost in cerebellar ataxia, with clinical outcomes readily measurable by methods known in the medical arts.

Huntington's disease (HD) is an autosomal dominant neurodegenerative disease characterized by a relentlessly progressive movement disorder with devastating psychiatric and cognitive deterioration. HD is associated with a consistent and severe atrophy of the neostriatum which is related to a marked loss of the GABAergic medium-sized spiny projection neurons, the major output neurons of the striatum. Intrastriatal injections of excitotoxins such as quinolinic acid (QA) mimic the pattern of selective neuronal vulnerability seen in HD. QA lesions result in motor and cognitive deficits which are among the major symptoms seen in HD. Thus, intrastriatal injections of QA have become a useful model of HD and can serve to evaluate novel therapeutic strategies aimed at preventing, attenuating, or reversing neuroanatomical and behavioral changes associated with HD. Because GABA-ergic neurons are characteristically lost in Huntington's disease, we contemplate treatment of Huntington's patients by transplantation of cell cultures enriched in GABA-ergic neurons derived according to the methods of this invention.

Epilepsy is also associated with excitotoxicity. Accordingly, GABA-ergic neurons derived according to this invention are contemplated for transplantation into patients suffering from epilepsy.

We also contemplate use of the cells of this invention in the treatment of various demyelinating and dysmyelinating disorders, such as Pelizaeus-Merzbacher disease, multiple sclerosis, various leukodystrophies, post-traumatic demyelination, and cerebrovascular (CVS) accidents, as well as various neuritis and neuropathies, particularly of the eye. We contemplate using cell cultures enriched in oligodendrocytes or oligodendrocyte precursor or progenitors, such cultures prepared and transplanted according to this invention to promote remyelination of demyelinated areas in the host.

We also contemplate use of the cells of this invention in the treatment of various acute and chronic pains, as well as for certain nerve regeneration applications (such as spinal cord injury). We also contemplate use of human stem cells for use in sparing or sprouting of photoreceptors in the eye.

The cells and methods of this invention are intended for use in a mammalian host, recipient, patient, subject or individual, preferably a primate, most preferably a human.

The following examples are provided for illustrative purposes only, and are not intended to be limiting.

EXAMPLES

Example 1

Media for Proliferating Neural Stem Cells

Proliferation medium was prepared with the following components in the indicated concentrations:

| Component | Final Concentration |
|---|---|
| 50/50 mix of DMEMlF-12 | 1X |
| glucose | 0.6% w/v |
| glutamine | 2 mM |
| NaHCO$_3$ | 3 mM |
| HEPES | 5 mM |
| apo-human transferrin (Sigma T-2252) | 100 µg/ml |
| human insulin (Sigma I-2767) | 25 µg/ml |
| putrescine (Sigma P-7505) | 60 µM |
| selenium (Sigma S-9133) | 30 nM |
| progesterone (Sigma P-6149) | 20 nM |
| human EGF (Gibco 13247-010) | 20 ng/ml |
| human bFGF (Gibco 13256-029) | 20 ng/ml |
| human LIF (R&D Systems 250-L) | 10 ng/ml |
| heparin (Sigma H-3149) | 2 µg/ml |

Example 2

Isolation of Human CNS Neural Stem Cells

Sample tissue from human embryonic forebrain was collected and dissected in Sweden and kindly provided by Huddinje Sjukhus. Blood samples from the donors were sent for viral testing. Dissections were performed in saline and the selected tissue was placed directly into proliferation medium (as described in Example 1). Tissue was stored at 4° C. until dissociated. The tissue was dissociated using a standard glass homogenizer, without the presence of any digesting enzymes. The dissociated cells were counted and seeded into flasks containing proliferation medium. After 5–7 days, the contents of the flasks are centrifuged at 1000 rpm for 2 min. The supernatant was aspirated and the pellet resuspended in 200 µl of proliferation medium. The cell clusters were triturated using a P200 pipetman about 100 times to break up the clusters. Cells were reseeded at 75,000–100,000 cells/ml into proliferation medium. Cells were passaged every 6–21 days depending upon the mitogens used and the seeding density. Typically these cells incorporate BrdU, indicative of cell proliferation. For T75 flask cultures (initial volume 20 ml), cells are "fed" 3 times weekly by addition of 5 ml of proliferation medium. We prefer Nunc flasks for culturing.

Nestin Staining for Proliferating Neurospheres

We stained for nestin ( a measure of proliferating neurospheres) as follows. Cells were fixed for 20 min at room temperature with 4% paraformaldehyde. Cells were washed twice for 5 min with 0.1 M PBS, pH 7.4. Cells were permeabilized for 2 min with 100% EtOH. The cells were then washed twice for 5 min with 0.1 M PBS. Cell preparations were blocked for 1 hr at room temperature in 5% normal goat serum ("NGS") diluted in 0.1M PBS, pH 7.4 and 1% Triton X-100 (Sigma X-100) for 1 hr at room temperature with gentle shaking. Cells were incubated with primary antibodies to human nestin (from Dr. Lars Wahlberg, Karolinska, Sweden, rabbit polyclonal used at 1:500) diluted in 1% NGS and 1% Triton X-100 for 2 hr at room temperature. Preparations were then washed twice for 5 min with 0.1 M PBS. Cells were incubated with secondary antibodies (pool of GAM/FITC used at 1:128, Sigma F-0257; GAR/TRITC used at 1:80, Sigma T-5268) diluted in 1% NGS and 1% Triton X-100 for 30 min at room temperature in the dark. Preparations are washed twice for 5 min with 0.1 M PBS in the dark. Preparations are mounted onto slides face down with mounting medium (Vectashield Mounting Medium, Vector Labs., H-1000) and stored at 4° C.

Figure 1:
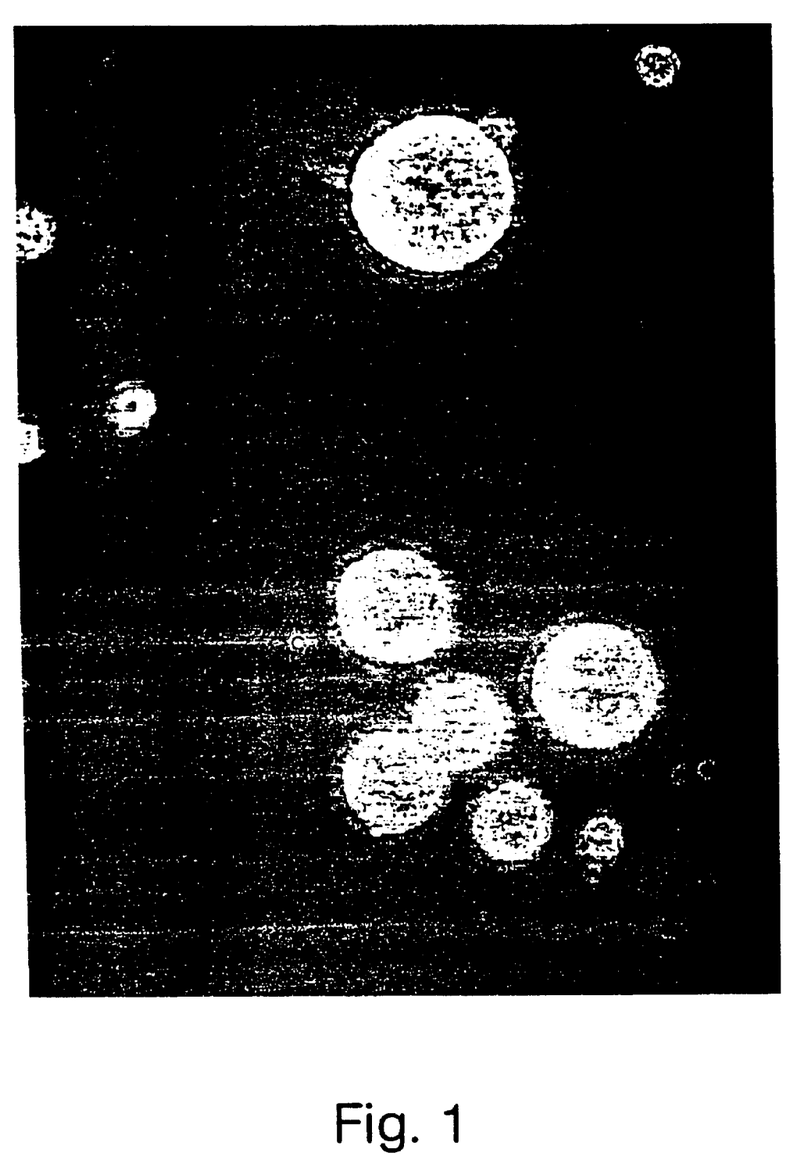
FIG. 1 shows a representation of spheres of proliferating 9FBr human neural stem cells (passage 6) derived from human forebrain tissue.
Figure 2A:
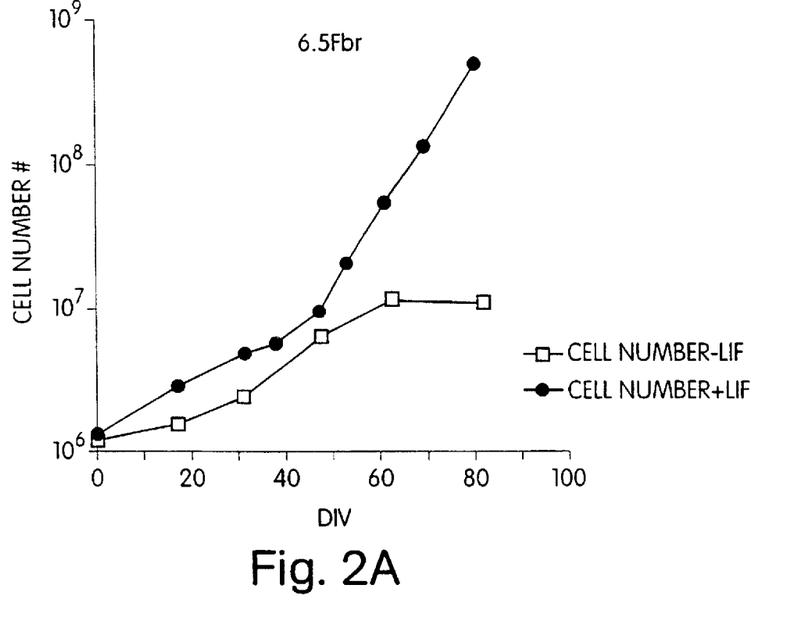
FIGS. 2A–2D, Panel A, shows a growth curve for a human neural stem cell line designated 6.5Fbr cultured in (a) defined media containing EGF, FGF and leukemia inhibitory factor ("LIF") (shown as closed diamonds), and (b) the same media but without LIF (shown as open diamonds); Panel B shows a growth curve for a human neural stem cell line designated 9Fbr cultured in (a) defined media containing EGF, FGF and LIF (shown as closed diamonds), and (b) the same media but without LIF (shown as open diamonds); Panel C shows a growth curve for a human neural stem cell line designated 9.5Fbr cultured in (a) defined media containing EGF, FGF and LIF (shown as closed diamonds), and (b) the same media but without LIF (shown as open diamonds); Panel D shows a growth curve for a human neural stem cell line designated 10.5Fbr cultured in (a) defined media containing EGF, FGF and leukemia inhibitory factor ("LIF") (shown as closed diamonds), and (b) the same media but without LIF (shown as open diamonds).
Figure 2B:
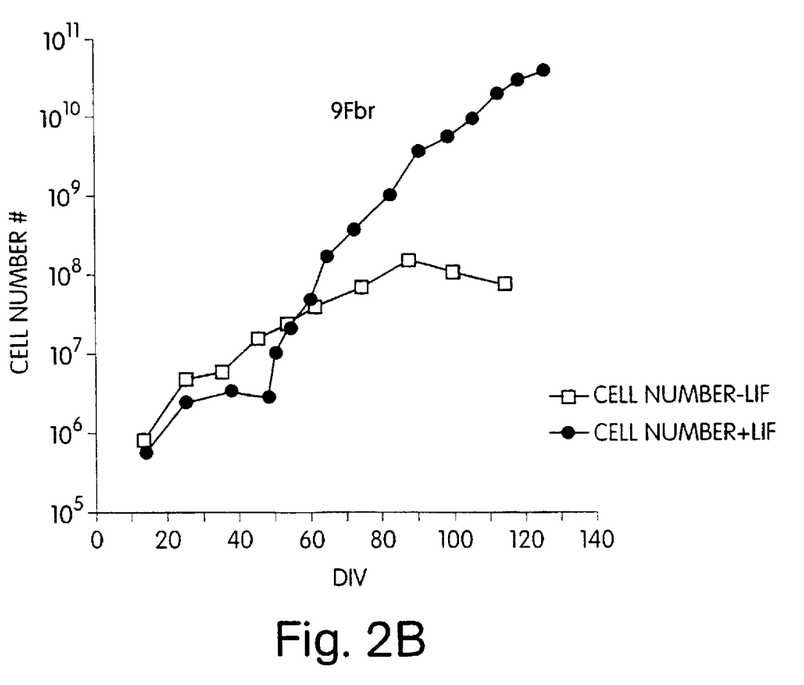
Figure 2C:
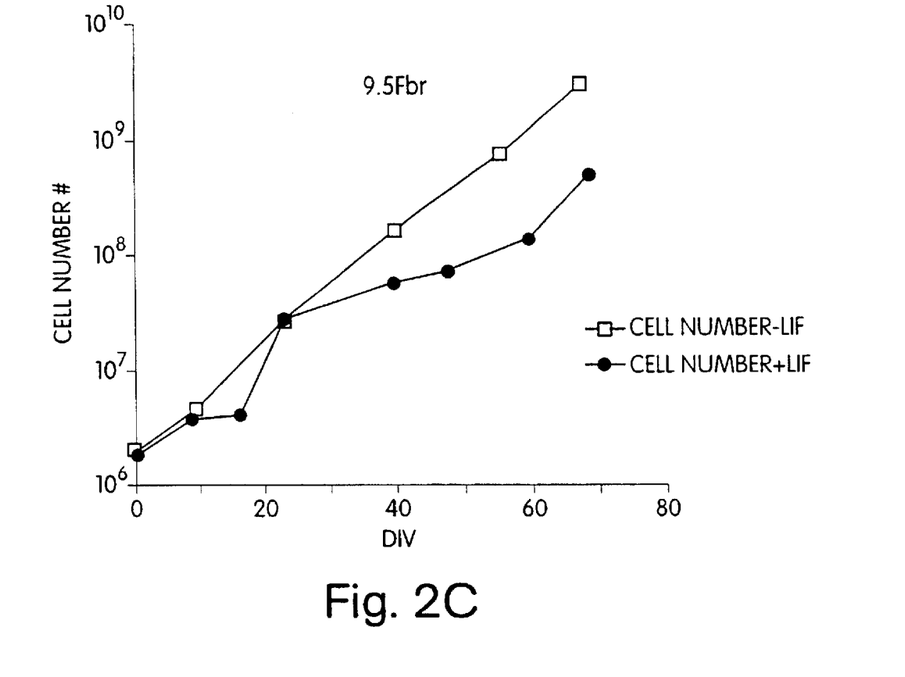
Figure 2D:
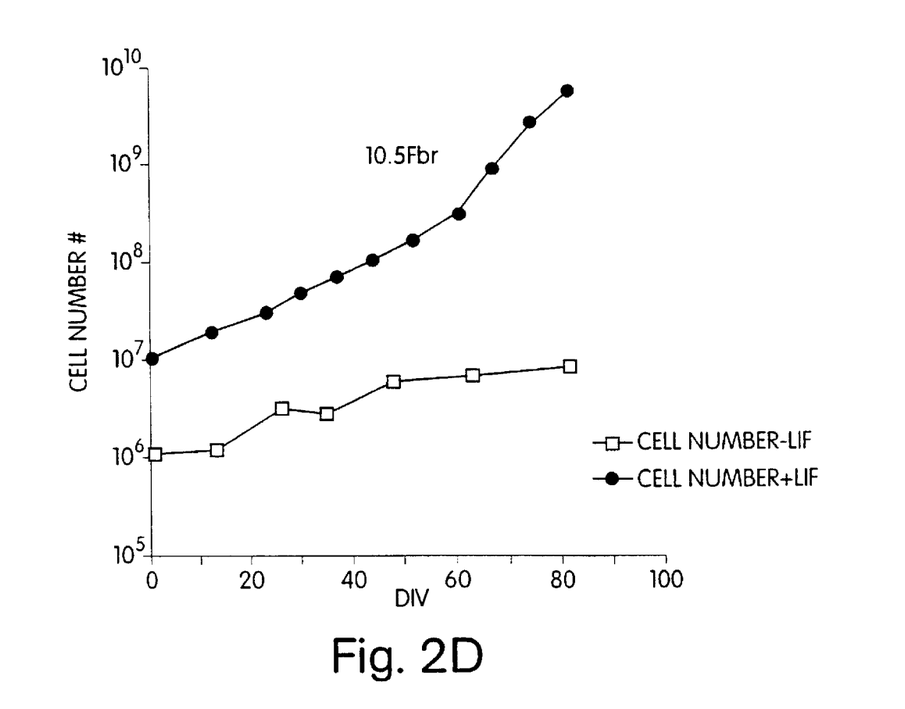

FIG. 1 shows a picture of proliferating spheres (here called "neurospheres") of human forebrain derived neural stem cells. We evaluated proliferation of 4 lines of human forebrain derived neural stem cells in proliferation medium as described above with LIF present of absent.

As FIG. 2 shows, in three of the four lines (6.5 Fbr, 9Fbr, and 10.5FBr), LIF significantly increased the rate of cell proliferation. The effect of LIF was most pronounced after about 60 days in vitro.

Figure 3:
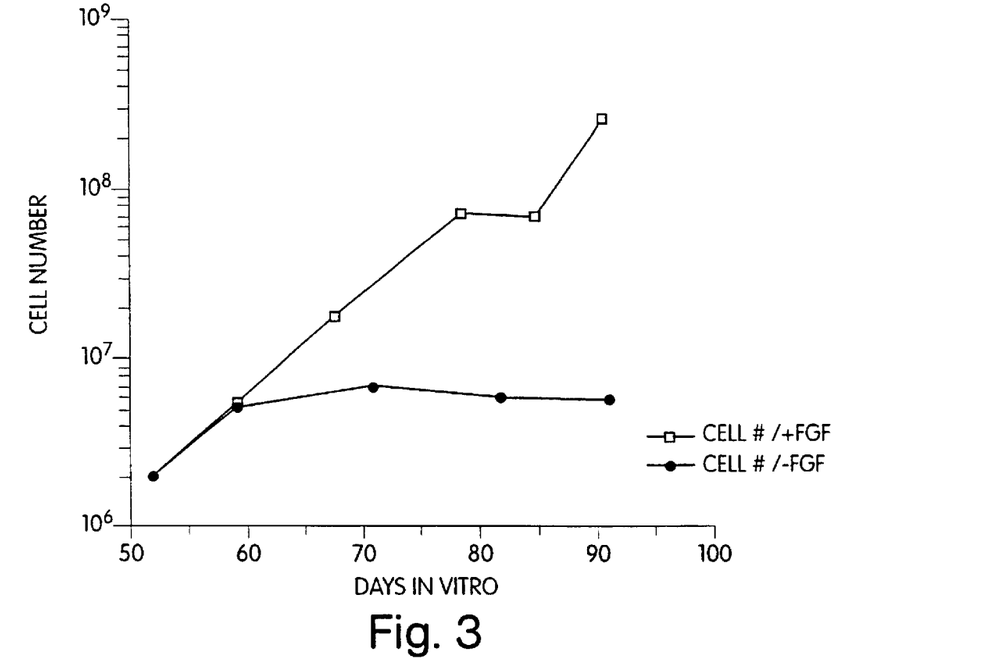
FIG. 3 shows a growth curve for a human neural stem cell line designated 9Fbr cultured in (a) defined media containing EGF and basic fibroblast growth factor ("bFGF") (shown as open diamonds), and (b) defined media with EGF but without bFGF (shown as closed diamonds).

We also evaluated the effect of bFGF on the rate of proliferation of human forebrain-derived neural stem cells. As FIG. 3 shows, in the presence of bFGF, the stem cells proliferation was significantly enhanced.

Example 3

Differentation of Human Neural Stem Cells

In a first differentiation protocol, the proliferating neurospheres were induced to differentiate by removal of the growth factor mitogens and LIF, and provision of 1% serum, a substrate and a source of ionic charges(e.g., glass cover slip covered with poly-omithine).

The staining protocol for neurons, astrocytes and oligodendrocytes was as follows:

β-Tubulin Stainin for Neurons

Cells were fixed for 20 min at room temperature with 4% paraformaldehyde. Cells were washed twice for 5 min with 0.1 M PBS, pH 7.4. Cells were permeabilized for 2 min with 100% EtOH. The cells were then washed twice for 5 min with 0.1 M PBS. Cell preparations were blocked for 1 hr at room temperature in 5% normal goat serum ("NGS") diluted in 0.1M PBS, pH 7.4. Cells were incubated with primary antibodies to β-tubulin (Sigma T-8660, mouse monoclonal; used at 1:1,000) diluted in 1% NGS for 2 hr at room temperature. Preparations were then washed twice for 5 min with 0.1 M PBS. Cells were incubated with secondary antibodies (pool of GAM/FITC used at 1:128, Sigma F-0257; GAR/TRITC used at 1:80, Sigma T-5268) diluted in 1% NGS for 30 min at room temperature in the dark. Preparations are washed twice for 5 min with 0.1 M PBS in the dark. Preparations are mounted onto slides face down with mounting medium (Vectashield Mounting Medium, Vector Labs., H-1000) and stored at 4° C.

In some instances we also stain with DAPI (a nuclear stain), as follows. Coverslips prepared as above are washed with DAPI solution (diluted 1:1000 in 100% MeOH, Boehringer Mannheim, # 236 276). Coverslips are incubated in DAPI solution for 15 min at 37° C.

O4 Staining for Oligodendrocytes Cells were fixed for 10 min at room temperature with 4% paraformaldehyde. Cells were washed three times for 5 min with 0.1 M PBS, pH 7.4. Cell preparations were blocked for 1 hr at room temperature in 5% normal goat serum ("NGS") diluted in 0.1M PBS, pH 7.4. Cells were incubated with primary antibodies to O4 (Boehringer Mannheim #1518 925, mouse monoclonal; used at 1:25) diluted in 1% NGS for 2 hr at room temperature. Preparations were then washed twice for 5 min with 0.1 M PBS. Cells were incubated with secondary antibodies, and further processed as described above for β-tubulin.

GFAP Staining for Astrocytes

Cells were fixed for 20 min at room temperature with 4% paraformaldehyde. Cells were washed twice for 5 min with 0.1 M PBS, pH 7.4. Cells were permeabilized for 2 min with 100% EtOH. The cells were then washed twice for 5 min with 0.1 M PBS. Cell preparations were blocked for 1 hr at room temperature in 5% normal goat serum ("NGS") diluted in 0.1M PBS, pH 7.4. Cells were incubated with primary antibodies to GFAP (DAKO Z 334, rabbit polyclonal; used at 1:500) diluted in 1% NGS for 2 hr at room temperature. Preparations were then washed twice for 5 min with 0.1 M PBS. Cells were incubated with secondary antibodies, and further processed as described above for β-tubulin. This differentiation protocol produced cell cultures enriched in neurons as follows:

| Cell Line | Passage | % GFAP Positive | % β-tubulin positive | % of neurons that are GABA positive |
| --- | --- | --- | --- | --- |
| 6.5 FBr | 5 | 15 | 37 | 20 |
| 9 FBr | 7 | 52 | 20 | 35 |
| 10.5 FBr | 5 | 50 | 28 | 50 |

We also evaluated the ability of a single cell line to differentiate consistently as the culture aged (i.e., at different passages), using the above differentiation protocol. The data are as follows:

| Cell Line | Passage | % GFAP Positive | % β-tubulin positive | % of neurons that are GABA positive |
| --- | --- | --- | --- | --- |
| 9 FBr | 7 | 53 | 20.4 | ND |
| 9 FBr | 9 | ND | 20.3 | 34.5 |
| 9 FBr | 15 | 62 | 17.9 | 37.9 |

We conclude from these data that cells will follow reproducible differentiation patterns irrespective of passage number or culture age.

Example 4

Differentation of Human Neural Stem Cells

In a second differentiation protocol, the proliferating neurospheres were induced to differentiate by removal of the growth factor mitogens and LIF, and provision of 1% serum, a substrate (e.g., glass cover slip or extracellular matrix components), a source of ionic charges (e.g., poly-ornithine) as well as a mixture of growth factors including 10 ng/ml PDGF A/B, 10 ng/ml CNTF, 10 ng/ml IGF-1, 10 μM forskolin, 30 ng/ml T3, 10 ng/ml LIF and 1 ng/ml NT-3. This differentiation protocol produced cell cultures highly enriched in neurons (i.e., greater than 35% of the differentiated cell culture) and enriched in oligodendrocytes.

Example 5

Differentation of Human Neural Stem Cells

In a third differentiation protocol, cell suspensions were initially cultured in a cocktail of hbFGF, EGF, and LIF, were then placed into altered growth media containing 20 ng/mL hEGF (GIBCO) and 10 ng/mL human leukemia inhibitory factor (hLIF) (R&D Systems), but without hbFGF. The cells initially grew significantly more slowly than the cultures that also contained hbFGF (see FIG. 3). Nonetheless, the cells continued to grow and were passaged as many as 22 times. Stem cells were removed from growth medium and induced to differentiate by plating on poly-omithine coated glass coverslips in differentiation medium supplemented with a growth factor cocktail (hPDGF A/B, hCNTF, hGF-1, forskolin, T3 and hNT-3). Surprisingly, GalC immunoreactivity was seen in these differentiated cultures at levels that far exceeded the number of O4 positive cells seen in the growth factor induction protocol described in Example 4.

Hence, this protocol produced differentiated cell cultures enrichment in oligodendrocytes. Neurons were only occasionally seen, had small processes, and appeared quite immature.

Example 6

Genetic Modification

We have conditionally immortalized a glioblast cell line derived from the human neural stem cells described herein, using the Mx-1 system described in WO 96/02646. In the Mx-1 system, the Mx-1 promoter drives expression of the SV40 large T antigen. The Mx-1 promoter is induced by interferon. When induced, large T is expressed, and quiescent cells proliferate.

Figure 4:
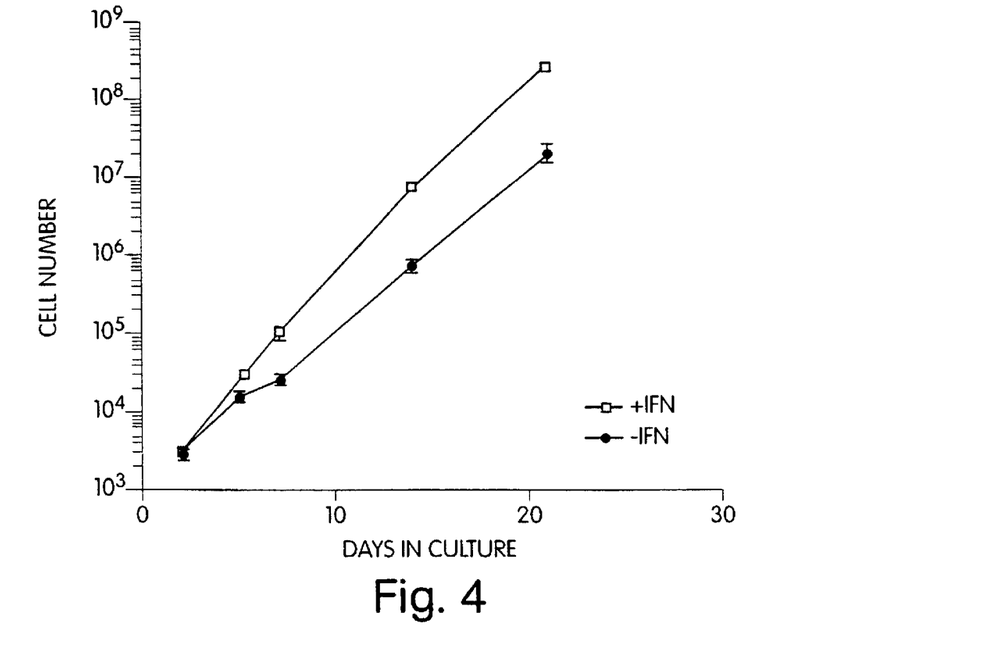
FIG. 4 shows a graph of cell number versus days in culture for an Mx-1 conditionally immortalized human glioblast line derived from a human neural stem cell line. The open squares denote growth in the presence of interferon, the closed diamonds denote growth in the absence of interferon.

Human glioblasts were derived from human forebrain neural stem cells as follows. Proliferating human neurospheres were removed from proliferation medium and plated onto poly-ornithine plastic (24 well plate) in a mixture of N2 with the mitogens EGF, bFGF and LIF, as well as 0.5% FBS. 0.5 ml of N2 medium and 1% FBS was added. The cells were incubated overnight. The cells were then transfected with p318 (a plasmid containing the Mx-1 promoter operably linked to the SV 40 large T antigen) using Invitrogen lipid kit (lipids 4 and 6). The transfection solution contained 6 μl/ml of lipid and 4 μl/ml DNA in optiMEM medium. The cells were incubated in transfection solution for 5 hours. The transfection solution was removed and cells placed into N2 and 1% FBS and 500 U/ml A/D interferon. The cells were fed twice a week. After ten weeks cells were assayed for large T antigen expression. The cells showed robust T antigen staining at this time. As FIG. 4 shows, cell number was higher in the presence of interferon than in the absence of interferon.

Large T expression was monitored using immunocytochemistry as follows. Cells were fixed for 20 min at room temperature with 4% paraformaldehyde. Cells were washed twice for 5 min with 0.1 M PBS, pH 7.4. Cells were permeabilized for 2 min with 100% EtOH. The cells were then washed twice for 5 min with 0.1 M PBS. Cell preparations were blocked for 1 hr at room temperature in 5% normal goat serum ("NGS") diluted in 0.1M PBS, pH 7.4. Cells were incubated with primary antibodies to large T antigen (used at 1: 10) diluted in 1% NGS for 2 hr at room temperature. We prepared antibody to large T antigen in house by culturing PAB 149 cells and obtaining the conditioned medium. Preparations were then washed twice for 5 min with 0.1 M PBS. Cells were incubated with secondary antibodies (goat-anti- mouse biotinylated at 1:500 from Vector Laboratories, Vectastain Elite ABC mouse IgG kit, PK-6102) diluted in 1% NGS for 30 min at room temperature. Preparations are washed twice for 5 min with 0.1 M PBS. Preparations are incubated in ABC reagent diluted 1:500 in 0.1 M PBS, pH 7.4 for 30 min at room temperature. Cells are washed twice for 5 min in 0.1 M PBS, pH 7.4, then washed twice for 5 min in 0.1 M Tris, pH 7.6. Cells are incubated in DAB (nickel intensification) for 5 min at room temperature. The DAB solution is removed, and cells are washed three to five times with dH20. Cells are stored in 50% glycerol50% 0.1 M PBS, pH 7.4.

Example 7

Encapsulation

If the human neural stem cells are encapsulated, then the following procedure may be used:

The hollow fibers are fabricated from a polyether sulfone (PES) with an outside diameter of 720 m and a wall thickness of a 100 m (AKZO-Nobel Wüppertal, Germany). These fibers are described in U.S. Pat. Nos. 4,976,859 and 4,968,733, herein incorporated by reference. The fiber may be chosen for its molecular weight cutoff. We sometimes use a PES#5 membrane which has a MWCO of about 280 kd. In other studies we use a PES#8 membrane which has a MWCO of about 90 kd.

The devices typically comprise:
1) a semipermeable poly (ether sulfone) hollow fiber membrane fabricated by AKZO Nobel Faser AG;
2) a hub membrane segment;
3) a light cured methacrylate (LCM) resin leading end; and
4) a silicone tether.

The semipermeable membrane used typically has the following characteristics:

| | |
|---|---|
| Internal Diameter | 500 + 30 m |
| Wall Thickness | 100 + 15 m |
| Force at Break | 100+ 15 cN |
| Elongation at Break | 44 + 10% |
| Hydraulic Permeability | 63 + 8(ml/min m$^2$ mmHg) |
| nMWCO (dextrans) | 280 + 20 kd |

The components of the device are commercially available. The LCM glue is available from Ablestik Laboratories (Newark, Del.); Luxtrak Adhesives LCM23 and LCM24). The tether material is available from Specialty Silicone Fabricators (Robles, Calif.). The tether dimensions are 0.79 mm OD×0.43 mm ID×length 202 mm. The morphology of the device is as follows: The inner surface has a permselective skin. The wall has an open cell foam structure. The outer surface has an open structure, with pores up to 1.5 m occupying 30+5% of the outer surface.

Fiber material is first cut into 5 cm long segments and the distal extremity of each segment sealed with a photopolymerized acrylic glue (LCM-25, ICI). Following sterilization with ethylene oxide and outgassing, the fiber segments are loaded with a suspension of between $10^4$–$10^7$ cells, either in a liquid medium, or a hydrogel matrix (e.g., a collagen solution (Zyderm©), alginate, agarose or chitosan) via a Hamilton syringe and a 25 gauge needle through an attached injection port. The proximal end of the capsule is sealed with the same acrylic glue. The volume of the device contemplated in the human studies is approximately 15–18 μl.

A silicone tether (Specialty Silicone Fabrication, Taunton, Mass.) (ID: 690 m; OD: 1.25 mm) is placed over the proximal end of the fiber allowing easy manipulation and retrieval of the device.

Example 8

Transplantation of Neural Stem Cells

We have transplanted human neural stem cells into rat brain and assessed graft viability, integration, phenotypic fate of the grafted cells, as well as behavioral changes associated with the grafted cells in lesioned animals.

Transplantation was performed according to standard techniques. Adult rats were anesthetized with sodium pentobarbitol (45 mg/kg, i.p.) And positioned in a Kopf stereotaxic instrument. A midline incision was made in the scalp and a hole drilled for the injection of cells. Rats received implants of unmodified, undifferentiated human neural stem cells into the left striatum using a glass capillary attached to a 10 μl Hamilton syringe. Each animal received a total of about 250,000–500,000 cells in a total volume of 2 μl. Cells were transplanted 1–2 days after passaging and the cell suspension was made up of undifferentiated stem cell clusters of 5–20 cells. Following implantation, the skin was sutured closed.

Animals were behaviorally tested and then sacrificed for histological analysis.

Example 9

Intraventricular EGF Delivery with Transplantation of Neural Stem Cells

Approximately 300,000 neural stem cells were transplanted as small neurospheres into the adult rat striatum close to the lateral ventricle using standard techniques. During the same surgery session, osmotic minipumps releasing either EGF (400 ng/day) or vehicle were also implanted in the striatum. The rats received EGF over a period of 7 days at a flow rate of 0.5 μL/hr, resulting in the delivery of 2.8 μg EGF in total into the lateral ventricle of each animal. Subsets of implanted rats were additionally immunosuppressed by i.p. cyclosporin injections (10 mg/kg/day). During the last 16 hours of pump infusion, the animals received injections of BrdU every three hours (120 mg/kg).

One week after transplantation, the animals were perfused with 4% para-formaldehyde and serial sections cut on a freezing microtome at 30 μm thickness. Brain sections were stained for astrocytes, oligodendrocytes, neuron, and undifferentiated progenitor cell markers. Minimal migration was demonstrated in adult CNS in the absence of EGF. Excellent survival of the 7 day old grafts was seen in rats receiving EGF as demonstrated by M2 inunumoreactivity, and grafts in EGF-treated animals were more extensive than in animals treated with vehicle alone. Furthermore, proliferation of host cells was observed upon EGF treatment. Animals receiving BrdU injections before sacrifice demonstrated an increased number of dividing cells in the treated ventricle, but not the adjoining ventricles.

Example 10

Treatment of Syringomyelia

Primary fetal transplants have been used to obliterate the syrinx formed around spinal cord injuries in patients. The neural stem cells described in this invention are suitable for replacement, because only a structural function would be required by the cells. Neural stem cells are implanted in the spinal cord of injured patients to prevent syrinx formation. Outcomes are measured preferably by MRI imaging. Clinical trial protocols have been written and could easily be modified to include the described neural stem cells.

Example 11

Treatment of Neurodegenerative Disease Using Progent of Human Neural Stem Cells Prolifereated in Vitro Cells are obtained from ventral mesencephalic tissue from a human fetus aged 8 weeks following routine suction abortion which is collected into a sterile collection apparatus. A 2×4×1 mm piece of tissue is dissected and dissociated as in Example 2. Neural stem cells are then proliferated. Neural stem cell progeny are used for neurotransplantation into a blood-group matched host with a neurodegenerative disease. Surgery is performed using a BRW computed tomographic (CT) stereotaxic guide. The patient is given local anesthesia suppiemencea with intravenously administered midazolam. The patient undergoes CT scanning to establish the coordinates of the region to receive the transplant. The injection cannula consists of a 17-gauge stainless steel outer cannula with a 19-gauge inner stylet. This is inserted into the brain to the correct coordinates, then removed and replaced with a 19-gauge infusion cannula that has been preloaded with 30 µl of tissue suspension. The cells are slowly infused at a rate of 3 µl/min as the cannula is withdrawn. Multiple stereotactic needle passes are made throughout the area of interest, approximately 4 mm apart. The patient is examined by CT scan postoperatively for hemorrhage or edema. Neurological evaluations are performed at various post-operative intervals, as well as PET scans to determine metabolic activity of the implanted cells.

Example 12

Genetic Modification of Neural Stem Cell Progeny Using Calcium Phosphate Transfection Neural stem cell progeny are propagated as described in Example 2. The cells are then transfected using a calcium phosphate transfection technique. For standard calcium phosphate transfection, the cells are mechanically dissociated into a single cell suspension and plated on tissue culture-treated dishes at 50% confluence (50,000–75,000 cells/cm$^2$) and allowed to attach overnight.

The modified calcium phosphate transfection procedure is performed as follows: DNA (15–25 µg) in sterile TE buffer (10 mM Tris, 0.25 mM EDTA, pH 7.5) diluted to 440 µl with TE, and 60 µl of 2M CaCl$_2$ (pH to 5.8 with 1M HEPES buffer) is added to the DNA/TE buffer. A total of 500 µl of 2×HeBS (HEPES-Buffered saline; 275 mM NaCl, 10 mM KCl, 1.4 mM Na$_2$HPO$_4$, 12 mM dextrose, 40 mM HEPES buffer powder, pH 6.92) is added dropwise to this mix. The mixture is allowed to stand at room temperature for 20 minutes. The cells are washed briefly with 1×HeBS and 1 ml of the calcium phosphate precipitated DNA solution is added to each plate, and the cells are incubated at 37° for 20 minutes. Following this incubation, 10 mls of complete medium is added to the cells, and the plates are placed in an incubator (37° C., 9.5% CO$_2$) for an additional 3–6 hours. The DNA and the medium are removed by aspiration at the end of the incubation period, and the cells are washed 3 times with complete growth medium and then returned to the incubator.

Example 13

Genetic Modification of Neural Stem Cell Progeny

Cells proliferated as in Examples 2 are transfected with expression vectors containing the genes for the FGF-2 receptor or the NGF receptor. Vector DNA containing the genes are diluted in 0.1×TE (1 mM Tris pH 8.0, 0.1 mM EDTA) to a concentration of 40 µg/ml. 22 µl of the DNA is added to 250 µl of 2×HBS (280 mM NaCl, 10 mM KCl, 1.5 mM Na$_2$HPO$_4$2H$_2$O, 12 mM dextrose, 50 mM HEPES) in a disposable, sterile 5 ml plastic tube. 31 µl of 2M CaCl$_2$ is added slowly and the mixture is incubated for 30 minutes at room temperature. During this 30 minute incubation, the cells are centrifuged at 800 g for 5 minutes at 4° C. The cells are resuspended in 20 volumes of ice-cold PBS and divided into aliquots of 1×10$^7$ cells, which are again centrifuged. Each aliquot of cells is resuspended in 1 ml of the DNA-CaCl$_2$ suspension, and incubated for 20 minutes at room temperature. The cells are then diluted in growth medium and incubated for 6–24 hours at 37° C. in 5%–7% CO$_2$. The cells are again centrifuged, washed in PBS and returned to 10 ml of growth medium for 48 hours.

The transfected neural stem cell progeny are transplanted into a human patient using the procedure described in Example 8 or Example 11, or are used for drug screening procedures as described in the example below.

Example 14

Screening of Drugs of Other Biological Agents for Effects of Multipotent Neural Stem Cells and Neural Stem Cell Progeny A. Effects of BDNF on Neuronal and Glial Cell Differentiation and Survival Precursor cells were propagated as described in Example 2 and differentiated as described in Example 4. At the time of plating the cells, BDNF was added at a concentration of 10 ng/ml. At 3, 7, 14, and 21 days in vitro (DIV), cells were processed for indirect immunocytochemistry. BrdU labeling was used to monitor proliferation of the neural stem cells. The effects of BDNF on neurons, oligodendrocytes and astrocytes were assayed by probing the cultures with antibodies that recognize antigens found on neurons (MAP-2, NSE, NF), oligodendrocytes (O4, GalC, MBP) or astrocytes (GFAP). Cell survival was determined by counting the number of immunoreactive cells at each time point and morphological observations were made. BDNF significantly increased the differentiation and survival of neurons over the number observed under control conditions. Astrocyte and oligodendrocyte numbers were not significantly altered from control values.

B. Effects of BDNF on the Differentiation of Neural Phenotypes

Cells treated with BDNF according to the methods described in Part A were probed with antibodies that recognize neural transmitters or enzymes involved in the synthesis of neural transmitters. These included TH, CHAT, substance P, GABA, somatostatin, and glutamate. In both control and BDNF-treated culture conditions, neurons tested positive for the presence of substance P and GABA. As well as an increase in numbers, neurons grown in BDNF showed a dramatic increase in neurite extension and branching when compared with control examples.

C. Identification of Growth-Factor Responsive Cells

Cells were differentiated as described in Example 4, and at 1 DIV approximately 100 ng/ml of BDNF was added. At 1, 3, 6, 12 and 24 hours after the addition of BDNF the cells were fixed and processed for dual label immunocytochemistry. Antibodies that recognize neurons (MAP-2, NSE, NF), oligodendrocytes (O4, GalC, MBP) or astrocytes (GFAP) were used in combination with an antibody that recognizes c-fos and/or other immediate early genes. Exposure to BDNF resulted in a selective increase in the expression of c-fos in neuronal cells.

D. Effects of BDNF on the Expression of Markers and Regulatory Factors During Proliferation and Differentiation Cells treated with BDNF according to the methods described in Part A are processed for analysis of the expression of regulatory factors, FGF-R1 or other markers.

E. Effects of Chlorpromazine on the Proliferation, Differentiation, and Survival of Growth Factor Generated Stem Cell Progeny Chlorpromazine, a drug widely used in the treatment of psychiatric illness, is used in concentrations ranging from 10 ng/ml to 1000 ng/ml in place of BDNF in Examples 14A to 14D above. The effects of the drug at various concentrations on stem cell proliferation and on stem cell progeny differentiation and survival is monitored. Alterations in gene expression and electrophysiological properties of differentiated neurons are determined.

What is claimed is:

1. A method for determining the effect of a biological agent comprising contacting a cell culture containing cells characterized by the presence or absence of a particular biological function or property with a biological agent, wherein the cell culture comprises:
   (a) a culture medium containing one or more growth factors effective for inducing multipotent central nervous system (CNS) neural stem cell proliferation; and
   (b) suspended in the culture medium, human multipotent CNS neural stem cells, wherein the cells have a doubling rate of 5–10 days;
   wherein the method further comprises determining whether the biological agent alters the presence or absence of the biological function or property ascribable to the cell culture.

2. The method of claim 1, wherein the cells comprise human forebrain-derived CNS neural stem cells.

3. The method of claim 1, wherein the cells comprise differentiated cells, derived from human central nervous system (CNS) neural stem cells, wherein greater than 10% of the differentiated cells are neurons, and wherein at least 20% of the neurons present are GABA positive.

4. The method of claim 3, wherein the cell culture comprises at least 20% neurons.

* * * * *